(12) United States Patent
Watanabe et al.

(10) Patent No.: US 6,743,959 B1
(45) Date of Patent: Jun. 1, 2004

(54) METHOD FOR THE DEHYDROGENATION OF TRIISOPROPYL BENZENE AND DIISOPROPYL BENZENE

(75) Inventors: Hiroyoshi Watanabe, Chiba (JP); Tatsumi Matsushita, Osaka (JP); Shinobu Aoki, Chiba (JP); Naoshi Nagai, Chiba (JP); Hisaharu Kuboyama, Kanagawa (JP)

(73) Assignee: Mitsui Chemicals, Inc., Tokyo (JP)

( * ) Notice: Subject to any disclaimer, the term of this patent is extended or adjusted under 35 U.S.C. 154(b) by 46 days.

(21) Appl. No.: 10/069,643

(22) PCT Filed: Aug. 30, 2000

(86) PCT No.: PCT/JP00/05870

§ 371 (c)(1),
(2), (4) Date: Feb. 28, 2002

(87) PCT Pub. No.: WO01/16062

PCT Pub. Date: Mar. 8, 2001

(30) Foreign Application Priority Data

Aug. 31, 1999 (JP) .............................. 11-244670
Nov. 11, 1999 (JP) .......................... 11-320411

(51) Int. Cl.[7] .............................. C07C 5/367
(52) U.S. Cl. ...................... 585/444; 585/445
(58) Field of Search ................ 585/444, 445

(56) References Cited

U.S. PATENT DOCUMENTS

| 3,429,941 A | 2/1969 | Kerr et al. |
| 3,907,916 A | 9/1975 | Soderquist et al. |
| 4,528,413 A | 7/1985 | Colvin et al. |
| 4,681,892 A | 7/1987 | Ingendoh et al. |

FOREIGN PATENT DOCUMENTS

| CN | 1161882 A | 10/1997 |
| EP | 0 177 832 A2 | 4/1986 |
| JP | 05-246908 | 9/1993 |
| WO | WO 91/06366 | 5/1991 |
| WO | WO 99/03806 | 1/1999 |

OTHER PUBLICATIONS

Fedorova, V.V. et al., Dehydrogenation of dialkylbenzenes, Khim. Khim, Teknol., 1974, pp 852–5, 17(6), Moscow, USSR.
Dimov, A., Synthesis of diispropenylbenzene, Ser. Khim Navuk, 1983, p. 1, (only).
Copy of Official Action Issued on Nov. 28, 2003, in counterpart Chinese Application No. 00814699.3.

*Primary Examiner*—Thuan D. Dang
(74) *Attorney, Agent, or Firm*—Burns, Doane, Swecker & Mathis, LLP

(57) ABSTRACT

An economical and industrial method for the dehydrogenation of triisopropyl benzene can be provided by carrying out the reaction employing a solid catalyst having an iron compound and potassium compound as major components or an iron compound, potassium compound, and magnesium compound as major components, as a dehydrogenating catalyst for producing diisopropyl isopropenyl benzene, isopropyl diisopropenyl benzene and/or triisopropenyl benzene from triisopropyl benzene. In the dehydrogenation of triisopropyl benzene or diisopropyl benzene, by carrying out an off-and-on reaction in which the above described solid catalyst is employed and with which a regeneration period with steam or oxygen or air is provided, an economical and industrial dehydrogenation method having an extended life of the catalyst can be provided and will have an industrial superiority.

36 Claims, 2 Drawing Sheets

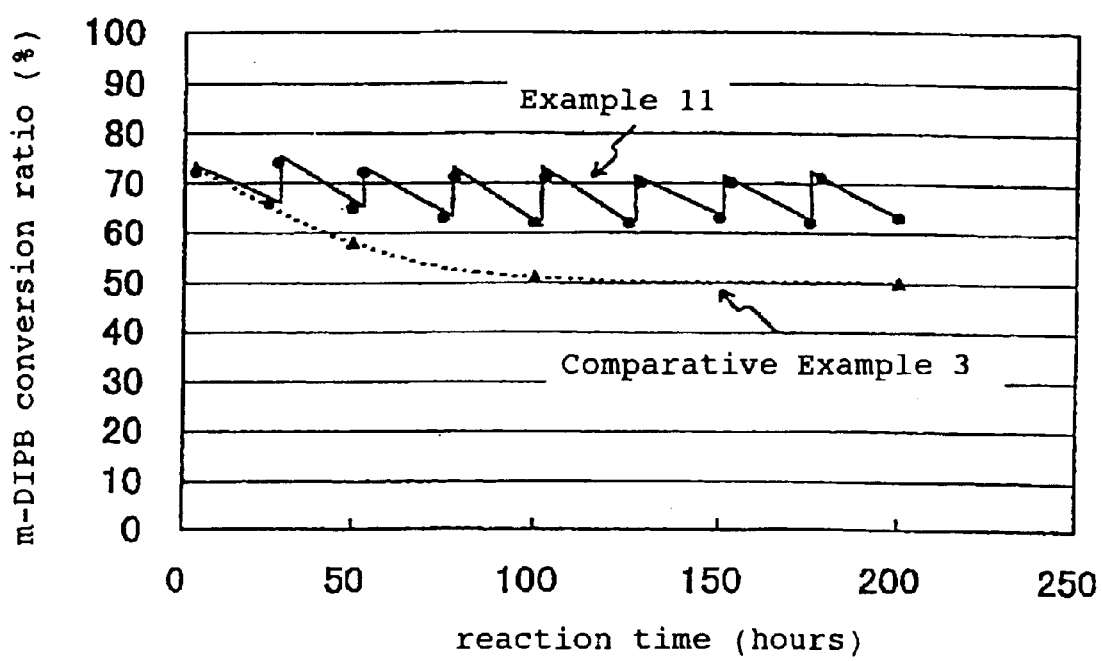
Fig. 1 m-DIPB conversion ratio over time

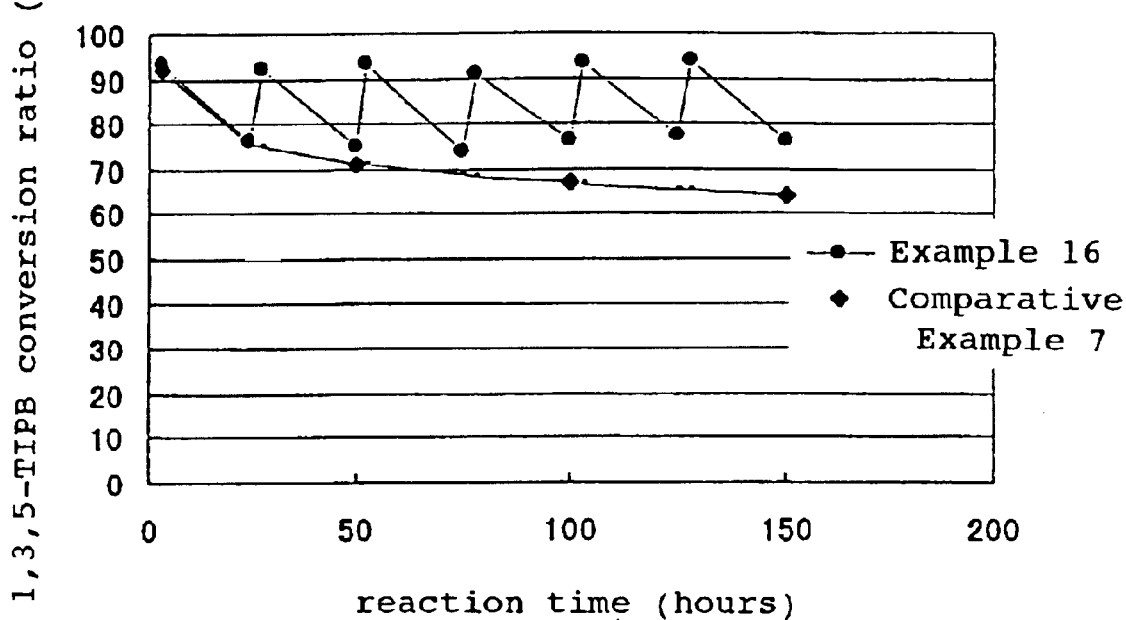
Fig. 2 1,3,5-TIPB conversion ratio over time

US 6,743,959 B1

METHOD FOR THE DEHYDROGENATION OF TRIISOPROPYL BENZENE AND DIISOPROPYL BENZENE

TECHNICAL FIELD

The present invention relates to a method for the dehydrogenation of triisopropyl benzene (hereinafter referred to as TIPB) and diisopropyl benzene.

Particularly, the present invention relates to a method for the dehydrogenation of TIPB in a vapor phase at an elevated temperature in the presence of steam to produce diisopropyl isopropenyl benzene (hereinafter referred to as DIPIPeB), isopropyl diisopropenyl benzene (hereinafter referred to as IPDIPeB) and/or triisopropenyl benzene (hereinafter referred to as TIPeB), and also to a method for the dehydrogenation of diisopropyl benzene in a vapor phase at an elevated temperature in the presence of steam to produce isopropenyl cumene and diisopropenyl benzene.

DIPIPeB, IPDIPeB, TIPeB, isopropenyl cumene, and diisopropenyl benzene are important compounds as intermediates in organic synthesis or as monomer components of functional polymers.

BACKGROUND ART

Until now, processes for the dehydrogenation of aromatic hydrocarbons to produce dehydrogenated aromatic hydrocarbons have been described in many publications in the past. For example, processes for the dehydrogenation of ethylbenzene to produce styrene are industrially carried out employing iron-based catalysts.

However, there is not known any method for the dehydrogenation of TIPB to economically produce DIPIPeB, IPDIPeB and/or TIPeB.

On the other hand, with respect to catalysts for dehydrogenating diisopropyl benzene, many proposals have been put forward until now. For example, there are known copper-chromium catalysts (CA, 14, 7383h), iron-chromium-potassium catalysts (Nissan Gardler Co.,Ltd. G64) (U.S. Pat. No. 3,429,941), iron-chromium-potassium-magnesium catalysts (CA, 81, 169877z), melt lithium or lead iodide catalysts (CA, 86, 55085n), and the like.

In addition, methods for purifying diisopropenyl benzene are also known (Japanese Patent Laid-Open No. 65029/1984 and Japanese Patent Laid-Open No. 204733/1985), but dehydrogenating catalysts and detailed reaction conditions are not described.

Catalysts thus far known cannot be yet satisfactory for industrial operation due to problems of the activity and catalyst life, and additionally have problems of requiring enormous costs of disposition as spent catalysts in view of environmental matter, since all the catalysts except for melt lithium or lead iodide catalysts contain chromium. Therefore, it is difficult to say that these catalysts are good industrial catalysts. Furthermore, in the case where melt lithium or lead iodide catalysts are employed, there are problems in methods of handling the catalysts in a melting state.

With respect to these reaction conditions, in the case of the production of styrene as a typical example of dehydrogenation reactions, the reaction is performed diluting with steam, on equilibrium grounds and for the purpose of removing carbonous material on the catalyst. The amount of steam is supplied at a weight ratio in the order of 1, relative to ethylbenzene as the raw material. With respect to the catalyst life, it is presumed that the catalyst is exchanged upon carrying out the regular maintenance once a year, but it seems that this cannot lead to industrialization at all, from information to date on the catalyst life in the reaction of dehydrogenating diisopropyl benzene or triisopropyl benzene.

Thus, in the case where problems exist in the catalyst life, there are required an increase in catalyst costs and disposition of spent catalysts resulting from catalyst exchange, or the shutdown of the operation or the opening of the reactor due to catalyst exchanging work, or the like, and therefore processes will become economically disadvantageous.

DISCLOSURE OF THE INVENTION

Subjects of the present invention are to provide an economical and industrial method for the dehydrogenation of TIPB and diisopropyl benzene and furthermore a continuously and stably operating method in which an environment-friendly catalyst not containing chromium as a catalyst component is employed and the deterioration of the catalyst is avoided.

The inventors have carried out intensive researches to solve problems described above, and obtained the finding that in the dehydrogenation of TIPB as the raw material, a reaction carried out employing a solid catalyst having an iron compound and potassium compound as major components or a solid catalyst having an iron compound, potassium compound, and magnesium compound as major components gives intended products DIPIPeB, IPDIPeB and/or TIPeB in a high yield and at a high selectivity, IA which has led to the completion of the present invention.

The inventors have also found that in the presence of a solid catalyst having an iron compound and potassium compound as major components or a solid catalyst having an iron compound, potassium compound, and magnesium compound as major components, a reaction in which a catalyst regeneration period with steam or oxygen or air is provided and the raw material diisopropyl benzene or triisopropyl benzene is fed intermittently can be carried out to obtain its intended products, namely, isopropenyl cumene and diisopropenyl benzene, or diisopropyl isopropenyl benzene, isopropyl diisopropenyl benzene and/or triisopropenyl benzene, in a high yield, with an improved life of the catalyst and at the same time a selectivity retained at a high level, which has led to the completion of the present invention.

In short, in a method for the dehydrogenation of TIPB in a vapor phase at an elevated temperature in the presence of steam and a solid catalyst to produce DIPIPeB, IPDIPeB and/or TIPeB, the present invention consists in a method for the dehydrogenation of TIPB in which the solid catalyst has an iron compound and potassium compound as major components. The present invention also consists in a method for the dehydrogenation of TIPB in which the solid catalyst has an iron compound, a potassium compound and a magnesium compound as major components.

Also, the present invention consists in a method for the dehydrogenation of triisopropyl benzene in a vapor phase at an elevated temperature in the presence of steam and a solid catalyst to produce diisopropyl isopropenyl benzene, isopropyl diisopropenyl benzene and/or triisopropenyl benzene, wherein:

i) the solid catalyst has an iron compound and a potassium compound as major components, or the solid catalyst has an iron compound, a potassium compound and a magnesium compound as major components, and ii) a combination of a reaction period and a catalyst regeneration period is made by feeding triisopropyl benzene intermittently.

In the reaction period, two components of the triisopropyl benzene and the steam contact with the solid catalyst, and in the catalyst regeneration period, only the steam contacts with the solid catalyst.

Further, the present invention consists in a method for the dehydrogenation of diisopropyl benzene in a vapor phase at an elevated temperature in the presence of steam and a solid catalyst to produce isopropenyl cumene and diisopropenyl benzene, wherein:

i) the solid catalyst has an iron compound and a potassium compound as major components, or the solid catalyst has an iron compound, a potassium compound, and a magnesium compound as major components, and ii) a combination of a reaction period and a catalyst regeneration period is made by feeding diisopropyl benzene intermittently.

In the reaction period, two components of the diisopropyl benzene and the steam contact with the solid catalyst, and in the catalyst regeneration period, only the steam contacts with the solid catalyst.

BRIEF DESCRIPTION OF DRAWINGS

FIG. 1 shows the conversion ratio over time of meta-diisopropyl benzene with or without the catalyst regeneration by steam.

FIG. 2 shows the conversion ratio over time of 1,3,5-triisopropyl benzene with or without the catalyst regeneration by steam.

BEST MODE FOR CARRYING OUT THE INVENTION

In the present invention, TIPB to be a raw material is obtained industrially as a by-product in producing cumene from propylene and benzene, and can be used as a raw material in the present invention by distillation purification.

As diisopropyl benzene to b a raw material can also be used meta-diisopropyl benzene and para-diisopropyl benzene. In the case of using meta-diisopropyl benzene, meta-isopropenyl cumene and meta-diisopropenyl benzene can be produced, and in the case using para-diisopropyl benzene, para-isopropenyl cumene and para-diisopropenyl benzene can be produced. These diisopropyl benzenes are obtained industrially as by-products in producing cumene from propylene and benzene, and can be used as a raw material in the present invention by distillation purification.

In the present invention, the raw material diisopropenyl benzene or TIPB is dehydrogenated in the presence of steam and a solid catalyst, and the solid catalyst is a solid catalyst having an iron compound and potassium compound as major components or a solid catalyst having an iron compound, potassium compound, and magnesium compound as major components.

As an example of the iron compound herein, iron oxide is usually used. As potassium compound, potassium carbonate, potassium hydroxide, potassium oxide, potassium nitrate, and the like can be used. As examples of magnesium compounds, magnesium oxide, magnesium carbonate, magnesium nitrate, and the like can be exemplified.

In a solid catalyst having an iron compound and potassium compound as major components, preferable percentages of the iron compound and potassium compound (% by weight) are 35 to 85% as $Fe_2O_3$ and 10 to 55% as $K_2CO_3$. In a solid catalyst having an iron compound, potassium compound, and magnesium compound as major components, preferable percentages are 35 to 85% as $Fe_2O_3$, 10 to 55% as $K_2CO_3$, and 1 to 15% as $MgCO_3$.

Additionally, besides an iron compound and potassium compound as major components, or besides an iron compound, potassium compound, and magnesium compound as major components, a solid catalyst used in the present invention can contain at least one compound selected from the group consisting of alkali metal compounds, alkaline earth metal compounds, rare earth metal compounds, molybdenum compounds, zirconium compounds, zinc compounds, manganese compounds, copper compounds, which is more preferable in terms of activity and selectivity. A preferable content of these compounds is 0.1 to 20% as oxides thereof.

As examples of alkali metal compounds, oxides, carbonates, hydroxides, nitrates, and the like of lithium, sodium, rubidium, cesium can be exemplified. As examples of alkaline earth metal compounds, oxides, carbonates, hydroxides, nitrates, and the like of calcium, magnesium, strontium, barium can be exemplified. As examples of rare earth metal compounds, oxides, sulfides, halides, hydroxides, nitrates, and the like of scandium, yttrium, lanthanum, cerium, samarium, and the like can be exemplified. As examples of molybdenum compounds, zirconium compounds, zinc compounds, manganese compounds and copper compounds, oxides, nitrates, halides, and the like of molybdenum, zirconium, zinc, manganese or copper can be exemplified, respectively.

These solid catalysts are readily available on the market. As a solid catalyst having an iron compound and potassium compound as major components, for example, G-64 I, G-64 F, G-84 B of Nissan Gardler Catalyst Co.,Ltd. can be used. As a solid catalyst having an iron compound, potassium compound, and magnesium compound as major components which can be preferably used, for example, G-64 J, G-64 JX, Regular G-84 C, G-84, G-84 E, Styromax-4, Styromax-5, and Styromax-Plus of Nissan Gardler Catalyst Co.,Ltd., and the like can be used in the case of the dehydrogenation of TIPB. In the case of the dehydrogenation of diisopropyl benzene, for example, G-64 J, G-64 JX. Regular G-84 C, G-84 C, G-84 D, G-84 E, Styromax-1, Styromax-3, Styromax-4, Styromax-5, Styromax-plus of Nissan Gardler Catalyst Co.,Ltd., and the like can be used.

On the dehydrogenation of TIPB, it is preferable that the temperature of the catalyst layer in a reactor is maintained in the range of 480 to 650° C., and preferably 510 to 600° C., and more preferably 520 to 580° C. In the description of the invention, "catalyst layer" means a zone which contains a catalyst, and includes not only "layer" in the narrow sense, but any arrangement of the catalyst, such as honeycomb and fluidized bed. If the temperature of the catalyst layer is at a lower temperature than 480° C., it is disadvantageous in that the reaction is slow even if the reaction takes place, while if the reaction is carried out at a higher temperature than 650° C., it is disadvantageous in that it may be likely to cause problems of resulting in the deterioration of the catalyst, and furthermore decomposing the raw material and the products and decreasing the yield, and the like. In the dehydrogenation reaction of diisopropyl benzene, it is preferable that the temperature of the catalyst layer in a reactor is maintained in the range of 500 to 650° C., and preferably 510 to 600° C., and more preferably 520 to 580° C. If the temperature of the catalyst layer is at a lower temperature than 500° C., it is disadvantageous in that the reaction is slow even if the reaction takes place, while if the reaction is carried out at a higher temperature than 650° C., it is disadvantageous in that it may be likely to cause problems of resulting in the deterioration of the catalyst, and furthermore decomposing the raw material and the products and decreasing the yield, and the like.

A reactor to be used for the dehydrogenation of TIPB or diisopropyl benzene is not specifically limited, and includes, for example, isothermal reactors, adiabatic reactors, and the like. In the case of an isothermal reactor, it is suitable to set up the temperature of the catalyst layer at 510 to 600° C. On the other hand, in the case of an adiabatic reactor which is often used for usual dehydrogenation of ethyl benzene, good results can be obtained when the temperature of the catalyst layer is made isothermal by means of setting up the inlet temperature of the catalyst layer at a temperature below 580° C., and additionally splitting the catalyst layer into two to three layers, and divided feeding of heating steam, and the like.

The amount of feeding TIPB to the catalyst layer, as expressed by liquid hourly space velocity LHSV, is preferably in the range of 0.01 to 1.4, more preferably 0.01 to 1.0, and further preferably 0.05 to 0.5. The amount of feeding diisopropyl benzene to the catalyst layer, as expressed by liquid hourly space velocity LHSV, is preferably in the range of 0.01 to 1.4, more preferably 0.1 to 1.0, and further preferably 0.2 to 0.8.

In the present invention, "in the presence of steam" means to feed steam to the catalyst layer in a reactor together with the raw material, i.e., TIPB or diisopropyl benzene. In the dehydrogenation reaction of TIPB, the amount of feeding steam to the catalyst layer together with the raw material TIPB is preferably in the range of 5 to 80 times, and more preferably 10 to 60 times, and even more preferably 20 to 50 times, based on weight ratio larger than TIPB. In the dehydrogenation of diisopropyl benzene, the amount of feeding steam is preferably in the range of 3 to 60 times, based on weight ratio larger than diisopropyl benzene. A smaller amount of steam used than that in these ranges is disadvantageous in that it may be likely that in addition to low activities of the catalyst, the deterioration of the catalyst due to coking becomes remarkable. On the other hand, a larger amount of steam used than that in these ranges is also disadvantageous in that although the catalyst has a good activity and the deterioration of the catalyst can be suppressed, it becomes not only disadvantageous energetically, but also worse in volumetric efficiency of the reactor. Furthermore, at a large amount of steam, for example, in the case of a weight ratio as described above of 70, although the mechanism is not clear, it is disadvantageous in that the use of an excess steam results in destabilizing the conversion ratio of the catalyst and gradually loosing the activity.

In both case of the dehydrogenation reactions of TIPB and of diisopropyl benzene, a lower pressure of the reaction pressure is suitable in terms of equilibrium, and the reaction pressure is normally preferably in the range of 0.01 to 0.5 MPa, and more preferably 0.03 to 0.2 MPa, in absolute pressure.

For the purpose of stable storage of a mixture liquid of DIPIPeB, IPDIPeB and/or TIPeB obtained by the dehydrogenation of TIPB or a mixture liquid of isopropenyl cumene and diisopropenyl benzene obtained by the dehydrogenation of diisopropyl benzene, a polymerization inhibitor can be added to it.

Distillation of the mixture liquid can give single component liquids which are fractionated into DIPIPeB, IPDIPeB, TIPeB components, or single component liquids which are fractionated into isopropenyl cumene, diisopropenyl benzene components. Distillation towers which can be employed in distillation are not specifically limited, and include, for example, packed towers, plate towers, bubble cap towers, and the like. Distilling modes are not specifically limited, and include, for example, continuous types, and batch types, and the like.

For the purpose of stable storage of these single component liquids of DIPIPeB, IPDIPeB, TIPeB, isopropenyl cumene, diisopropenyl benzene, a polymerization inhibitor can be similarly added, as described above.

As examples of polymerization inhibitors can be exemplified diphenyl picryl hydrazyl, 2,4-dinitrophenol, 4-hydroxy-2,2,6,6-tetramethylpiperidine N-oxide, N-(3-N-oxyanilino-1,3-dimethyl butylydene) aniline oxide, para-benzoquinone, para-tert-butyl catechol, nitoroso benzene, picric acid, dithiobenzoyl disulfide, copper (II) chloride, and the like.

The amount of using these polymerization inhibitors is not specifically limited, and normally preferably in the range of 0.01 ppm to 1%, and more preferably 0.1 to 1000 ppm, and even more preferably 1 to 500 ppm, based on the weight of a mixture liquid of DIPIPeB, IPDIPeB, TIPeB obtained by the dehydrogenation of TIPB, or a mixture liquid of isopropenyl cumene and diisopropenyl benzene obtained by the dehydrogenation of diisopropyl benzene, or these single component liquids fractionated by distillation. These polymerization inhibitors can be used alone or in combination.

As shown in FIG. 1, the deterioration degree of the catalyst will be revealed by plotting conversion ratios of meta-diisopropyl benzene (m-DIPB) on the ordinate and elapsed periods of the reaction on the abscissa. In FIG. 1, when the reaction is carried out at an amount of steam to meta-diisopropyl benzene of 10, the conversion ratio is gradually decreased until approximately 100 hours if a regeneration period is not provided, and appears to be stable later, but seems to show a somewhat decrease. On the other hand, when the reaction is intermittently carried out with providing regeneration periods, the catalyst activity can be returned to the fresh condition each time and a high activity can be again exhibited. Accordingly, it is clear that the reaction carried out with regeneration periods will give a higher conversion and an enhanced yield of the products, as compared with the converted amount of the raw material at a reaction time of 200 hours.

As such regenerating operation, only by discontinuing feeding diisopropyl benzene in this period, the catalyst regeneration can be readily achieved. Furthermore, any problem is not caused when the amount of feeding steam and the temperature are the quite same as the reaction conditions. In addition, the regeneration time for a period of the order of 0.2 to 1 hour is sufficient. As indicated in FIG. 1, when the reaction is carried out for 25 hours and then the regeneration is carried out for 1 hour, it is shown that the catalyst activity is regenerated and the regenerated catalyst again displays a reaction performance equal to the initial activity.

In the catalyst regeneration, it is possible to employ oxygen or air, instead of steam. In this case, feeding into a reactor not only diisopropyl benzene but also water (steam) has to be discontinued, but taking waste water treatment and the like into account, a regeneration method with oxygen or air is also achievable. The amount of feeding oxygen is preferably 1000 to 15000, and more preferably 2000 to 12000, and even more preferably 3700 to 9000, on GHSV. The amount of feeding air is preferably 2000 to 30000, and more preferably 4000 to 25000, and even more preferably7500 to 20000, on GHSV. Feeding at a smaller amount than that in these ranges has a disadvantage in that it is difficult for the catalyst regeneration to proceed, a larger amount is disadvantageous in terms of cost.

Taking account of operations like repeating reaction periods and catalyst regeneration periods, it is possible to carry out an efficient production by a process in which a reactor has a single line and diisopropyl benzene is fed intermittently, and by a continuous process having two or more lines, that is, in which a phase in which all the lines are on the stage of the catalyst regeneration at the same time is not provided, and the periods of the catalyst regeneration are staggered in each line.

With respect to requirements concerning deciding when the reaction is ceased and the catalyst regeneration is started, there are not specific limitations, determination can be made as appropriate, considering operating circumstances of the reaction equipment, the operation schedule, or the operation cost, or the like. For example, it is possible to control the operation by commencing the catalyst regeneration when the catalyst activity has been decreased by 20 to 30 percent from the initial activity.

The length of the catalyst regeneration period is also determined as appropriate. According to the present invention, in the case where the regeneration is carried out in particular with steam, it is possible to shorten to a great extent the period until restarting the reaction after discontinuing the reaction. The reason is that in conventional art, the catalyst regeneration is carried out after once shutting down the plant and stopping the raw material and steam upon regenerating the catalyst, but according to the present invention, it is possible to carry out the reaction and the catalyst regeneration sequentially without shutdown and while the condition of feeding steam is remained unchanged.

As an example, the dehydrogenation of diisopropyl benzene has been explained here. Also in the case of the dehydrogenation of TIPB, repeating the reaction and the catalyst regeneration is similarly effective as described above.

The methods according to the present invention will be explained specifically by means of Example as follows, to which the present invention is not to be limited. All the reactions in the following examples were carried out under atmospheric pressure.

EXAMPLE 1

This Example was carried out employing a reaction tube which had a system of uniformly heating the outside of a stainless steel tube having an inner diameter of 21.5 mm. This reaction tube was filled with 40 ml of a G-84 catalyst ground to a particle size of 0.5 mm, Nissan Gardler Catalyst Co. ,Ltd. (containing iron-potassium-magnesium-cerium-molybdenum-calcium as catalyst components), and then on the catalyst layer, with 30 ml of steatite balls having a particle size of 2 mm to form a preheating layer.

Before starting the reaction, the temperatures of the catalyst layer and the preheating layer were heated at 560° C. by an electric furnace. Then, 1.3.5-TIPB at 6 g/hr and water at 240 g/hr were fed to the preheating layer for gasification and vaporization prior to introducing them into the catalyst layer. In this case, the liquid hourly space velocity LHSV value of 1,3,5-TIPB was 0.16.

From 3 hours after starting the reaction, reaction tube outflow was collected to analyze the weight and composition. Results showed that the conversion ratio of 1,3,5-TIPB was 90%, 1,3-diisopropyl-5-isopropenyl benzene (hereinafter referred to as 1,3-DIP-5-IPeB) was obtained in a yield of 12%, 1-isopropyl-3,5-diisopropenyl benzene (hereinafter referred to as 1-IP-3.5-DIPeB) in a yield of 23%, and 1,3,5-TIPeB in a yield of 54%.

EXAMPLE 2

This Example was carried out in a way similar to that in Example 1, except for changing the catalyst to a Styromax-4 catalyst, Nissan Gardler Catalyst Co.,Ltd. (containing iron-potassium-magnesium-and-other-elements as catalyst components). Results showed that the conversion ratio of 1,3,5-TIPB was 99%, 1,3-DIP-5-IPeB was obtained in a yield of 1%, 1-IP-3,5-DIPeB in a yield of 11%, and 1,3,5-TIPeB in a yield of 80%.

EXAMPLE 3

This Example was carried out in a way similar to that in Example 1, except for changing the catalyst to a Styromax-Plus catalyst, Nissan Gardler Catalyst Co.,Ltd. (containing iron-potassium-magnesium-and-other-elements as catalyst components). Results showed that the conversion ratio of 1,3,5-TIPB was 99%, 1,3-DIP-5-IPeB was obtained in a yield of 1%, 1-IP-3,5-DIPeB in a yield of 10, and 1,3,5-TIPeB in a yield of 82%.

EXAMPLE 4

This Example was carried out in a way similar to that in Example 1, except for changing the catalyst to a G64 JX catalyst, Nissan Gardler Catalyst Co.,Ltd. (containing iron-potassium-magnesium-cerium-molybdenum as catalyst components). Results showed that the conversion ratio of 1,3,5-TIPB was 88%, 1,3-DIP-5-IPeB was obtained in a yield of 16%, 1-IP-3,5-DIPeB in a yield of 28%, and 1,3,5-TIPeB in a yield of 40%.

COMPARATIVE EXAMPLE 1

This Comparative Example was carried out in a way similar to that in Example 1, except for changing the catalyst to an N-401 catalyst. Nikki Chemical Co. (containing chromium-magnesium-alumina as catalyst components). Results showed that the conversion ratio of 1,3,5-TIPB was 25%, 1,3-DIP-5-IPeB was obtained in a yield of 14%, 1-IP-3,5-DIPeB in a yield of 8%, and 1,3,5-TIPeB in a yield of 1%.

COMPARATIVE EXAMPLE 2

This Comparative Example was carried out in a way similar to that in Example 1, except for changing the catalyst to an ST-200 catalyst, Sakai Chemical Industry Co. Ltd., (containing copper-chromium as major components). Results showed that the conversion ratio of 1,3,5-TIPB was 23%, 1,3-DIP5-IPeB was obtained in a yield of 13%, 1-IP-3,5-DIPeB in a yield of 6%, and 1,3,5-TIPeB in a yield of 0%.

EXAMPLE 6

This Example was carried out in a way similar to that in Example 2, except for changing the temperature of the catalyst layer to temperatures as indicated below (Table 1). Results are given in Table 1.

TABLE 1

| Catalyst Layer Temperature (° C.) | 1,3,5-TIPB Conversion Ratio (%) | 1,3-DIP-5-IPeB Yield (%) | 1-IP-3,5-DIPeB Yield (%) | 1,3,5-TIPeB Yield (%) |
| --- | --- | --- | --- | --- |
| 520 | 50 | 25 | 23 | 1 |
| 540 | 95 | 8 | 21 | 62 |

TABLE 1-continued

| Catalyst Layer Temperature (° C.) | 1,3,5-TIPB Conversion Ratio (%) | 1,3-DIP-5-IPe B Yield (%) | 1-IP-3,5-DIPe B Yield (%) | 1,3,5-TIPeB Yield (%) |
|---|---|---|---|---|
| 560 | 99 | 1 | 10 | 80 |
| 600 | 100 | 0 | 9 | 78 |

EXAMPLE 7

This Example was carried out in a way similar to that in Example 2, except for changing the liquid hourly space velocity LHSV of 1,3.5 -TIPB to those as indicated below (Table 2) (with remaining the ratio of the flow rates of 1,3,5-TIPB/water unchanged). Results are given in Table 2.

TABLE 2

| LHSV (Hr$^{-1}$) | 0.01 | 0.16 | 0.5 | 1 |
|---|---|---|---|---|
| 1,3,5-TIPB Conversion Ratio (%) | 100 | 99 | 75 | 50 |
| 1,3-DIP-5-IPeB Yield (%) | 1 | 1 | 26 | 25 |
| 1-IP-3,5-DIPeB Yield (%) | 12 | 10 | 25 | 23 |
| 1,3,5-TIPeB Yield (%) | 82 | 80 | 20 | 1 |

EXAMPLE 8

This Example was carried out in a way similar to that in Example 7, except for changing the liquid hourly space velocity LHSV of 1,3,5-TIPB to 1.5 (with remaining the ratio of the flow rates of 1,3,5-TIPB/water unchanged). Results showed that the conversion ratio of 1,3,5-TIPB was 15%, 1,3-DIP-5-IPeB was obtained in a yield of 7%, 1-IP-3,5-DIPeB in a yield of 6%, and 1,3,5-TIPeB in a yield of 0%.

EXAMPLE 9

This Example was carried out in a way similar to that in Example 3, except for changing the feeding ratio (Wt/Wt) of steam and 1,3,5-TIPB to those as indicated below (Table 3). Results are given in Table 3.

TABLE 3

| Water/1,3,5-TIPB (wt/wt) | 10 | 20 | 40 | 60 |
|---|---|---|---|---|
| 1,3,5-TIPB Conversion Ratio (%) | 73 | 90 | 99 | 100 |
| 1,3-DIP-5-IPeB Yield (%) | 23 | 13 | 1 | 1 |
| 1-IP-3,5-DIPeB Yield (%) | 23 | 26 | 10 | 11 |
| 1,3,5-TIPeB Yield (%) | 18 | 43 | 80 | 83 |

EXAMPLE 10

This Example was carried out in a way similar, to that in Example 9, except for changing the feeding ratio (Wt/Wt) of steam and 1,3,5-TIPB to 2. Results showed that the conversion ratio of 1,3,5-TIPB was 30%, 1,3-DIP-5-IPeB was obtained in a yield of 13%, 1-IP-3,5-DIPeB in a yield of 12%, and 1,3,5-TIPeB in a yield of 0%.

EXAMPLE 11

This Example was carried out employing a reaction tube which had a system of uniformly heating the outside of a stainless steel tube having an inner diameter of 21.5 mm. This reaction tube was filled with 20 ml (24.5 g) of a Styromax-plus catalyst ground to a particle size of 0.5 to 2 mm, Nissan Gardler Catalyst Co.,Ltd. (containing iron-potassium-magnesium-and-other-elements as catalyst components), and then on the catalyst layer, with 30 ml of steatite balls having a particle size of 2 mm to form a preheating layer.

Before starting the reaction, the temperatures of the catalyst layer and the preheating layer were heated at 540° C. by an electric furnace. Then, meta-diisopropyl benzene (hereinafter referred to as m-DIPB) at 6 g/hr and water at 60 g/hr were fed to the preheating layer for gasification and vaporization prior to introducing them into the catalyst layer. In this case, the liquid hourly space velocity LHSV value was 0.35.

After the reaction was carried out in a continuous mode for 25 hours, only the feeding of m-DIPB was stopped for one hour to form a catalyst regeneration period, with remaining the flow rate of water and the reactor temperature unchanged. Then, m-DIPB was again fed to start the reaction. These reaction-and-catalyst regeneration periods were repeated to carry out a series of reactions of 200 hours in total (excluding the periods of the catalyst regeneration), and the conversion ratio of m-DIPB was determined. For reaction performance, reaction tube outflows were collected to analyze their weights and compositions at 3 hours and 25 hours after starting each reaction. The relationship between the conversion ratio of m-DIPB and the reaction time is shown in Table 4 and FIG. 1.

COMPARATIVE EXAMPLE 3

This Comparative Example was carried out in a way similar to that in Example 11, except for carrying out a continuous reaction without catalyst regeneration periods. Results from analysis of outflows for the weight and composition at 3, 50, 100, and 200 hours after starting the reaction showed a conversion ratio of m-TIPB of 73, 58, 51, and 50%, respectively.

EXAMPLE 12

This Example was carried out in a way similar to that in Example 11, except for using para-diisopropyl benzene instead of m-DIPB used in Example 11. Results are given in Table 4.

COMPARATIVE EXAMPLE 4

This Comparative Example was,carried out in a way similar to that in Example 12, except for carrying out a continuous reaction without catalyst regeneration periods. Results from analysis of outflows for the weight and composition at 3, 50, 100, and 200 hours after starting the reaction showed a conversion ratio of para-diisopropyl benzene of 75, 55, 53, and 53%, respectively.

EXAMPLE 13

This Example was carried out in a way similar to that in Example 11, except for feeding oxygen, instead of steam, during the catalyst regeneration periods (GHSV=5000). Results are given in Table 4.

EXAMPLE 14

This Example was carried out in a way similar to that in Example 11, except for feeding air, instead of steam, during the catalyst regeneration periods (GHSV 20000). Results are given in Table 4.

EXAMPLE 15

This Example was carried out in a way similar to that in Example 11, except for arranging the reaction equipment of Example 11 in two lines and having each of the catalyst regeneration periods staggered by 13 hours to form an alternate catalyst regeneration period. Results are given in Table 4.

TABLE 4

| Reaction Times (Hr) | 3 | 25 | 28 | 50 | 53 | 75 | 78 | 100 | 103 | 125 | 128 | 150 | 153 | 175 | 178 | 200 |
|---|---|---|---|---|---|---|---|---|---|---|---|---|---|---|---|---|
| Diisopropyl benzene Conversion Ratio (%) | | | | | | | | | | | | | | | | |
| Example 11 | 72 | 66 | 74 | 65 | 72 | 63 | 71 | 62 | 71 | 62 | 70 | 63 | 70 | 62 | 71 | 63 |
| Comparative Example 3 | 73 | — | — | 58 | — | — | — | 51 | — | — | — | — | — | — | — | 50 |
| Example 12 | 74 | 63 | 72 | 63 | 70 | 62 | 70 | 61 | 69 | 60 | 69 | 61 | 70 | 61 | 70 | 61 |
| Comparative Example 4 | 75 | — | — | 55 | — | — | — | 53 | — | — | — | — | — | — | — | 53 |
| Example 13 | 71 | 65 | 72 | 65 | 71 | 62 | 71 | 61 | 71 | 60 | 70 | 61 | 70 | 62 | 71 | 61 |
| Example 14 | 72 | 63 | 71 | 62 | 70 | 62 | 72 | 59 | 71 | 59 | 70 | 60 | 71 | 59 | 71 | 61 |
| Example 15 | 71 | 68 | 72 | 67 | 70 | 65 | 69 | 64 | 69 | 64 | 68 | 65 | 68 | 64 | 69 | 65 |

COMPARATIVE EXAMPLE 5

This Comparative Example was carried out under the same reaction conditions as those of Example 11, except for changing the catalyst to an N-401 catalyst, Nikki Chemical Co. (containing chromium-magnesium-alumina as catalyst components). Reaction tube outflows were collected to analyze the weight and composition from 3 hours after starting the reaction. Results showed that the conversion ratio of m-DIPB was 25%, meta-isopropenyl cumene was obtained in a yield of 7%, and meta-diisopropenyl benzene in a yield of 0%.

COMPARATIVE EXAMPLE 6

This Comparative Example was carried out in a way similar to that in Comparative Example 5, except for changing the catalyst to an ST-200 catalyst, Sakai Chemical Industry Co. Ltd., (containing copper-chromium as catalyst components). Results showed that the conversion ratio of m-DIPB was 23%, meta-isopropenyl cumene was obtained in a yield of 18%, and meta-diisopropenyl benzene in a yield of 2%.

EXAMPLE 16

This Example was carried out employing a reaction tube which had a system of uniformly heating the outside of a stainless steel tube having an inner diameter of 21.5 mm. This reaction tube was filled with 40 ml of an Styromax-plus catalyst ground to a particle size of 0.5 mm, Nissan Gardler Catalyst Co.,Ltd. (containing iron-potassium-magnesium-and-other-elements as catalyst components), and then on the catalyst layer, with 30 ml of steatite balls having a particle size of 2 mm to form a preheating layer.

Before starting the reaction, the temperatures of the catalyst layer and the preheating layer were heated at 560° C. by an electric furnace. Then, 1,3,5-triisopropyl benzene (hereinafter referred to as 1,3,5-TIPB) at 6 g/hr and water at 240 g/hr were fed to the preheating layer for gasification and vaporization prior to introducing them into the catalyst layer.

In this case, the liquid hourly space velocity LHSV value of 1,3,5-TIPB was 0.16.

After the reaction was carried out in a continuous mode for 25 hours, only the feeding of 1,3,5-TIPB was stopped for one hour to form a catalyst regeneration period, with remaining the flow rate of water and the reactor temperature unchanged. Then, 1,3,5-TIPB was again fed to start the reaction. These reaction-and-catalyst regeneration periods were repeated to carry out a series of reactions of 150 hours in total (excluding the periods of the catalyst regeneration), and the conversion ratio of 1,3,5-TIPB was determined. For reaction performance, reaction tube outflows were collected to analyze the weight and composition at 3 hours and 25 hours after starting each reaction. The relationship between the conversion ratio of 1,3,5-TIPB and the reaction time is shown in Table 5 and FIG. 2.

COMPARATIVE EXAMPLE 7

This Comparative Example was carried out in a way similar to that in Example 16, except for carrying out a continuous reaction without catalyst regeneration periods. Results from analysis of outflows for the weight and composition at 3, 50, 100, and 150 hours after starting the reaction showed a conversion ratio of 1,3,5-TIPB of 92, 71, 67, and 64%, respectively.

EXAMPLE 17

This Example was carried out in a way similar to that in Example 16, except for feeding air, instead of steam, during the catalyst regeneration periods (GHSV=10000). Results are given in Table 5.

EXAMPLE 18

This Example was carried out in a way similar to that in Example 16, except for arranging the reaction equipment of Example 16 in two lines and having each of their catalyst regeneration periods staggered by 13 hours to form an alternate catalyst regeneration period. Results are given in Table 5.

TABLE 5

| Reaction Times (Hr) | 3 | 25 | 28 | 50 | 53 | 75 | 78 | 100 | 103 | 125 | 128 | 150 |
|---|---|---|---|---|---|---|---|---|---|---|---|---|
| 1,3,5-Triisopropyl benzene Conversion Ratio (%) | | | | | | | | | | | | |
| Example 16 | 93 | 76 | 92 | 75 | 93 | 74 | 91 | 76 | 93 | 77 | 94 | 76 |
| Comparative Example 7 | 92 | — | — | 71 | — | — | — | 67 | — | — | — | 64 |

TABLE 5-continued

| Example 17 | 92 | 75 | 91 | 74 | 93 | 73 | 92 | 75 | 93 | 76 | 93 | 77 |
| Example 18 | 92 | 80 | 91 | 81 | 92 | 82 | 90 | 80 | 91 | 82 | 93 | 83 |

INDUSTRIAL APPLICABILITY

An economical and industrial method for the dehydrogenation of triisopropyl benzene can be provided by carrying out the reaction employing a solid catalyst having an iron compound and potassium compound as major components or an iron compound, potassium compound, and magnesium compound as major components, as, a dehydrogenating catalyst for producing diisopropyl isopropenyl benzene, isopropyl diisopropenyl benzene and/or triisopropenyl benzene from triisopropyl benzene.

In the dehydrogenation of triisopropyl benzene or diisopropyl benzene, by carrying out an off-and-on reaction in which the above described solid catalyst which is environment-friendly and does not contain chromium as a catalyst component is employed and with which a regeneration period with steam or oxygen or air is provided, an economical and industrial method for the dehydrogenation of diisopropyl benzene which has solved problems of conventional art and in particular has an extended life of the catalyst can be provided and will have an industrial superiority.

What is claimed is:

1. A method of dehydrogenating triisopropyl benzene in a vapor phase at an elevated temperature in the presence of steam and a solid catalyst to produce diisopropyl isopropenyl benzene, isopropyl diisopropenyl benzene and/or triisopropenyl benzene, characterized in that said solid catalyst is mainly composed of an iron compound and a potassium compound and does not contain chromium as a catalyst component, and the feed amount of the steam which is fed together with the raw material triisopropyl benzene is between 10 and 60 times in weight ratio as large as the feed amount of the triisopropyl benzene.

2. The method according to claim 1, wherein triisopropyl benzene is 1,3,5-triisopropyl benzene.

3. The method according to claim 1, wherein the solid catalyst is mainly composed of an iron compound, a potassium compound and a magnesium compound.

4. The method according to claim 3, characterized in that the solid catalyst further comprises at least one compound selected from the group consisting of alkali metal compounds other than the potassium compound, alkaline earth metal compounds other than the magnesium compound, rare earth metal compounds, molybdenum compounds, zirconium compounds, zinc compounds, manganese compounds and copper compounds.

5. The method according to claim 1, characterized in that the solid catalyst further comprises at least one compound selected from the group consisting of alkali metal compounds other than the potassium compound, alkaline earth metal compounds, rare earth metal compounds, molybdenum compounds, zirconium compounds, zinc compounds, manganese compounds and copper compounds.

6. The method according to claim 5, wherein the temperature of the dehydrogenation reaction is between 480 and 650° C.

7. The method according to claim 1, wherein the temperature of the dehydrogenation reaction is between 480 and 650° C.

8. The method according to claim 1, wherein the feed amount of the triisopropyl benzene is between 0.01 and 1.4 on LHSV.

9. The method according to claim 1, wherein the feed amount of the triisopropyl benzene is between 0.01 and 1.0 on LHSV.

10. The method according to claim 1, wherein the feed amount of the triisopropyl benzene is between 0.01 and 1.4 on LHSV.

11. The method according to claim 1, wherein the feed amount of the triisopropyl benzene is between 0.01 and 1.0 on LHSV.

12. A method of dehydrogenating triisopropyl benzene in a vapor phase at an elevated temperature in the presence of steam and a solid catalyst to produce diisopropyl isopropenyl benzene, isopropyl diisopropenyl benzene and/or triisopropenyl benzene, characterized in that said solid catalyst is mainly composed of an iron compound and a potassium compound and does not contain chromium as a catalyst component, and in that a combination of a reaction period and a catalyst regeneration period is made by feeding triisopropyl benzene intermittently, in said reaction period, two components of the triisopropyl benzene and the steam contacting with the solid catalyst, the feed amount of the steam which is fed together with the raw material triisopropyl benzene being between 10 and 60 times in weight ratio as large as the feed amount of the triisopropyl benzene, and in said catalyst regeneration period, only the steam, oxygen or air contacting with the solid catalyst.

13. The method according to claim 12, wherein the feed amount of the triisopropyl benzene is between 0.01 and 1.4 in liquid hourly space velocity LHSV.

14. The method according to claim 12, wherein the feed amount of the triisopropyl benzene is between 0.01 and 1.0 in liquid hourly space velocity LHSV.

15. The method according to claim 14, wherein the solid catalyst is mainly composed of an iron compound, a potassium compound and a magnesium compound.

16. The method according to claim 12, wherein the solid catalyst is mainly composed of an iron compound, a potassium compound and a magnesium compound.

17. The method according to claim 16, characterized in that the solid catalyst further comprises at least one compound selected from the group consisting of alkali metal compounds other than the potassium compound, alkaline earth metal compounds other than the magnesium compound, rare earth metal compounds, molybdenum compounds, zirconium compounds, zinc compounds, manganese compounds and copper compounds.

18. The method according to claim 12, wherein triisopropyl benzene is 1,3,5-triisopropyl benzene.

19. The method according to claim 12, characterized in that the solid catalyst further comprises at least one compound selected from the group consisting of alkali metal compounds other than the potassium compound, alkaline earth metal compounds, rare earth metal compounds, molybdenum compounds, zirconium compounds, zinc compounds, manganese compounds and copper compounds.

20. The method according to claim 12, wherein the feed amount of the triisopropyl benzene is between 0.01 and 1.4 in liquid hourly space velocity LHSV.

21. The method according to claim 12, wherein the feed amount of the triisopropyl benzene is between 0.01 and 1.0 in liquid hourly space velocity LHSV.

22. The method according to claim 21, wherein the solid catalyst is mainly composed of an iron compound, a potassium compound and a magnesium compound.

23. A method of dehydrogenating diisopropyl benzene in a vapor phase at an elevated temperature in the presence of steam and a solid catalyst to produce isopropenyl cumene and diisopropenyl benzene, characterized in that said solid catalyst is mainly composed of an iron compound and potassium compound and does not contain chromium as a catalyst component, and in that a combination of a reaction period and a catalyst regeneration period is made by feeding diisopropyl benzene intermittently, in said reaction period, two components of the diisopropyl benzene and the steam contacting with the solid catalyst, the feed amount of the steam which is fed together with the raw material diisopropyl benzene being between 3 and 60 times in weight ratio as large as the feed amount of the diisopropyl benzene, and in said catalyst regeneration period, only the steam, oxygen or air contacting with the solid catalyst.

24. The method according to claim 23, wherein the feed amount of the diisopropyl benzene is between 0.01 and 1.4 in liquid hourly space velocity LHSV.

25. The method according to claim 24, wherein the solid catalyst is mainly composed of an iron compound, a potassium compound and a magnesium compound.

26. The method according to claim 23, wherein the feed amount of the diisopropyl benzene is between 0.1 and 1.0 in liquid hourly space velocity LHSV.

27. The method according to claim 23, wherein the solid catalyst is mainly composed of an iron compound, a potassium compound and a magnesium compound.

28. The method according to claim 27, wherein diisopropyl benzene is meta-diisopropyl benzene, and isopropenyl cumene and diisopropenyl benzene are meta-isopropenyl cumene and meta-diisopropenyl benzene, respectively.

29. The method according to claim 27, wherein diisopropyl benzene is para-diisopropyl benzene, and isopropenyl cumene and diisopropenyl benzene are para-isopropenyl cumene and para-diisopropenyl benzene, respectively.

30. The method according to claim 27, characterized in that the solid catalyst further comprises at least one compound selected from the group consisting of alkali metal compounds other than the potassium compound, alkaline earth metal compounds other than the magnesium compound, rare earth metal compounds, molybdenum compounds, zirconium compounds, zinc compounds, manganese compounds and copper compounds.

31. The method according to claim 23, wherein diisopropyl benzene is meta-diisopropyl benzene, and isopropenyl cumene and diisopropenyl benzene are meta-isopropenyl cumene and meta-diisopropenyl benzene, respectively.

32. The method according to claim 23, wherein diisopropyl benzene is para-diisopropyl benzene, and isopropenyl cumene and diisopropenyl benzene are para-isopropenyl cumene and para-diisopropenyl benzene, respectively.

33. The method according to claim 23, characterized in that the solid catalyst further comprises at least one compound selected from the group consisting of alkali metal compounds other than the potassium compound, alkaline earth metal compounds, rare earth metal compounds, molybdenum compounds, zirconium compounds, zinc compounds, manganese compounds and copper compounds.

34. The method according to claim 23, wherein the feed amount of the diisopropyl benzene is between 0.01 and 1.4 in liquid hourly space velocity LHSV.

35. The method according to claim 34, wherein the solid catalyst is mainly composed of an iron compound, a potassium compound and a magnesium compound.

36. The method according to claim 23, wherein the feed amount of the diisopropyl benzene is between 0.1 and 1.0 in liquid hourly space velocity LHSV.

* * * * *